(12) United States Patent
Song

(10) Patent No.: US 8,083,747 B2
(45) Date of Patent: Dec. 27, 2011

(54) MAXILLARY SINUS BONE GRAFT METHOD USING THE SINUS LIFT DRILL (SLD) AND HYDRAULIC EFFECT

(76) Inventor: Young-wan Song, Seoul (KR)

( * ) Notice: Subject to any disclaimer, the term of this patent is extended or adjusted under 35 U.S.C. 154(b) by 427 days.

(21) Appl. No.: 12/190,494

(22) Filed: Aug. 12, 2008

(65) Prior Publication Data
US 2010/0042222 A1 Feb. 18, 2010

(51) Int. Cl.
*A61B 17/58* (2006.01)
*A61B 17/60* (2006.01)
*A61F 2/00* (2006.01)

(52) U.S. Cl. ............... 606/92; 606/93; 606/94

(58) Field of Classification Search ............ 606/92, 606/93, 94; 433/174, 175, 180, 215
See application file for complete search history.

(56) References Cited

U.S. PATENT DOCUMENTS

| 5,989,025 | A * | 11/1999 | Conley | 433/76 |
| 7,125,253 | B2 * | 10/2006 | Kitamura et al. | 433/173 |
| 2003/0194380 | A1 * | 10/2003 | Szymaitis | 424/50 |
| 2007/0042326 | A1 * | 2/2007 | Cardoso et al. | 433/229 |
| 2009/0274996 | A1 * | 11/2009 | Miller | 433/215 |
| 2009/0292288 | A1 * | 11/2009 | Hung | 606/84 |

* cited by examiner

*Primary Examiner* — Thomas C. Barrett
*Assistant Examiner* — Christine Nelson
(74) *Attorney, Agent, or Firm* — John K. Park; Park Law Firm

(57) ABSTRACT

The invention relates to a dental implant method using a tissue punch, sinus lift drill (SLD) and hydraulic effect which places a bone graft and embed a dental implant at a maxillary sinus area where there is not sufficient bone to embed a dental implant. The method includes: removing mucoperiosteum having a size of an dental implant to be implanted at a alveolar crest area using a tissue punch, drilling a maxillary sinus floor easily and safely without causing damage to a maxillary sinus membrane by inserting a sinus lift drill which has a protruding member that is elastically installed in the body so as to protrude from and retract in the longitudinal direction of the body, elevating a maxillary sinus membrane by the hydraulic effect (injecting graft adjacent to the drilled maxillary sinus floor); and installing the implant in an inside portion of the drilled maxillary sinus floor.

3 Claims, 10 Drawing Sheets

MAXILLARY SINUS BONE GRAFT METHOD USING THE SINUS LIFT DRILL (SLD) AND HYDRAULIC EFFECT

BACKGROUND OF THE INVENTION

1. Field of the Invention

The present invention relates to a dental implant method, and more particularly, to a sinus bone graft method using a sinus lift drill (SLD) and hydraulic effect which can easily and simply drill a maxillary sinus floor without causing damage to a maxillary sinus membrane so that a dental implant can be installed in a short time.

2. Description of the Related Art

Recently, dental implant surgery for installing artificial teeth has been rapidly popularized in dental clinics.

However, in case of some dental patients, the structure of the oral cavity makes it difficult to perform the implant surgery, so that the dental implant surgery becomes complicated, or some dentists often decline to give such a patient medical treatment.

In particular, the dentist has difficulty in performing the implant installation in the case where a small amount of bone matrix remains in the posterior area near the maxillary sinus. In this case, the maxillary sinus membrane is elevated to secure a space, a bone graft is placed in the secured space, and a dental implant is embedded in this space. This method is classified into a vertical approach and a lateral approach.

First, the vertical approach is a method that is used when a bone matrix in a target area for implant surgery is secure to some extent (the thickness of the bone matrix is 4 mm or more), in which method the maxilla is tapped several times with an osteotome (a chisel and hammer), forming a hole having a diameter from 2 mm to 3 mm, and graft bone material is inserted little by little through the hole. This method has an advantage in that a patient has little edema after the surgery because of the narrow target surgery area. However, since the dentist cannot directly see the maxillary sinus membrane, he/she has to perform surgery very carefully, checking the membrane with X-ray images, which takes a lot of time, thereby prolonging the surgery, and in that the patient experiences severe discomfort due to the tapping during the surgery.

Next, the lateral approach is a method that is used when a very small amount of bone matrix remains in a target area for implant surgery (the thickness of the bone matrix is 3 mm or less), in which method the maxilla is drilled to form a hole (window) in a lateral side so as to elevate the maxillary sinus membrane, and bone grafting is carried out through the hole. The method had an advantage in that, since the dentist can lift the maxillary sinus membrane, directly viewing the same during the surgery, the membrane is seldom damaged, in that, even if damage to the membrane occurs, post-treatment for dealing with the situation is possible, and the desired quantity of bone graft can be placed quickly at one time, so that the processing is implemented quickly. However, the method also has a problem in that the surgery itself is difficult to perform, and a larger mucoperiosteal flap should be provided, so that severe edema may occur after the surgery. Accordingly, dentists avoid performing such a method in clinics.

Meanwhile, in addition to the above methods, a maxillary sinus elevation (or a maxillary sinus lift) method using a common implant drill as shown in FIG. 3 has been recently researched. The maxillary sinus elevation method has an advantage in that it is easy and fast to penetrate a maxillary sinus floor. However, at the moment that the maxillary sinus membrane is completely bored by the rotation of the drill blades, the tips of the drill blades are brought into contact with the maxillary sinus membrane, damaging the membrane by tearing or rolling. Therefore, the maxillary sinus elevation method using the drill is impossible to use.

Accordingly, there is a need to develop a maxillary sinus bone graft method using a sinus lift drill (SLD) and hydraulic effect which can simply penetrate the maxillary sinus floor without causing damage to the maxillary sinus membrane, thereby safely performing the implant surgery in a short surgery time.

SUMMARY OF THE INVENTION

The present invention has been made to solve the foregoing problems with the prior art, and therefore an aspect of the present invention is directed to a maxillary sinus bone graft method using a sinus lift drill (SLD) and hydraulic effect which can simply penetrate a maxillary sinus floor without causing damage to a maxillary sinus membrane, thereby safely installing an implant in a short surgery time.

According to an aspect of the present invention, the maxillary sinus bone graft method includes steps of: removing mucoperiosteum having a size (diameter) of a dental implant to be implanted at an alveolar crest area using a tissue punch drill without mucoperiosteal flap, penetrating a maxillary sinus floor easily and safely without causing damage to a maxillary sinus membrane by drilling a sinus lift drill which has a protruding member that is elastically installed in the body so as to protrude from and retract in the longitudinal direction of the body, lifting a maxillary sinus membrane by injecting graft adjacent to the penetrated maxillary sinus floor; and installing the implant in an inside portion of the same maxillary sinus floor.

Further, the graft is composed of a fluid substance, and the step of injecting the graft includes: storing the graft in an amount ranging from 0.3 cc to 0.5 cc in a syringe having a capacity of 1 cc; removing a needle from the leading end of the syringe; bring a nozzle of the syringe into close contact with an opening of the same hole; forcing the syringe into the same hole under predetermined pressure; and injecting the graft into the same hole using the hydraulic effect.

Alternatively, the graft is composed of a non-fluid substance, and the step of injecting a graft includes: mixing the graft with 0.4 cc of a physiological salt solution in a syringe having a volume of 1 cc; removing a needle from the leading end of the syringe; bringing a nozzle of the syringe into close contact with an opening of the same hole; forcing the syringe into the same hole under predetermined pressure; and injecting the graft into the same hole using the hydraulic effect.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Hereinafter, a maxillary sinus bone graft method using a sinus lift drill (SLD) and hydraulic effect according to the invention will be described more fully with reference to the accompanying drawings, in which exemplary embodiments thereof are shown.

Figure 1:
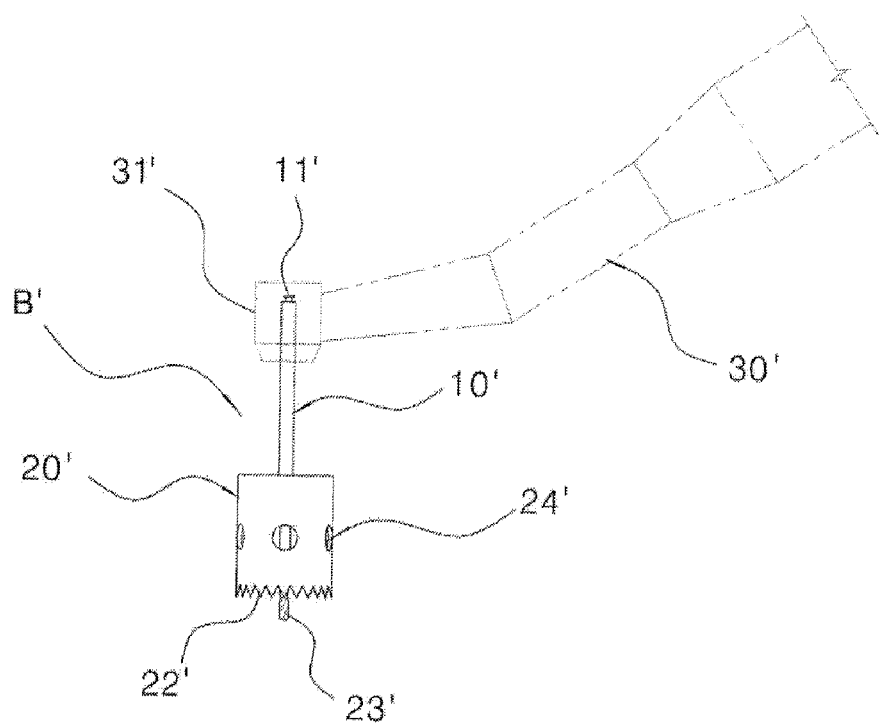
FIGS. 1 and 2 are views illustrating the operational states of a drill for forming a hole in the mucoperiosteum according to the present invention.
Figure 2:
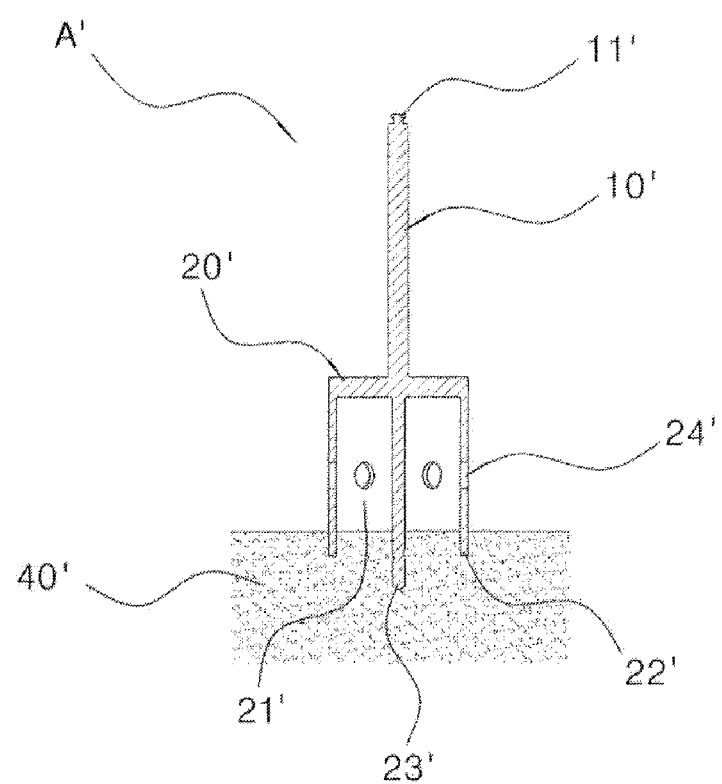
Figure 3:
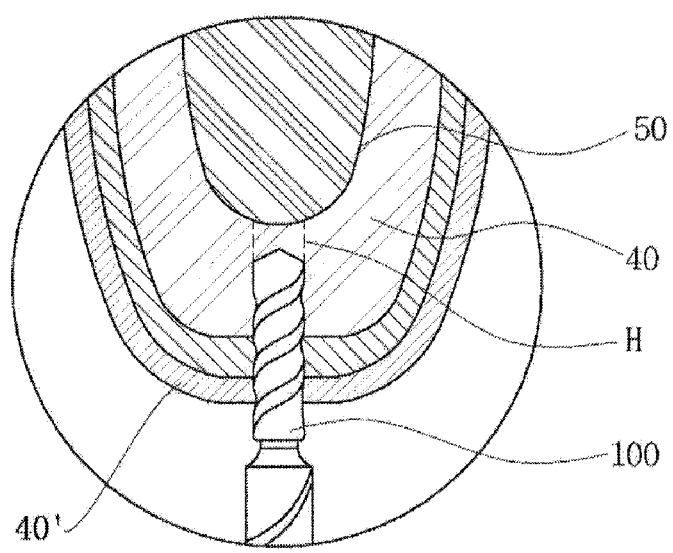
FIG. 3 is a cross-sectional view illustrating the state in which a maxilla is drilled to form a hole by a twist drill.
Figure 4:
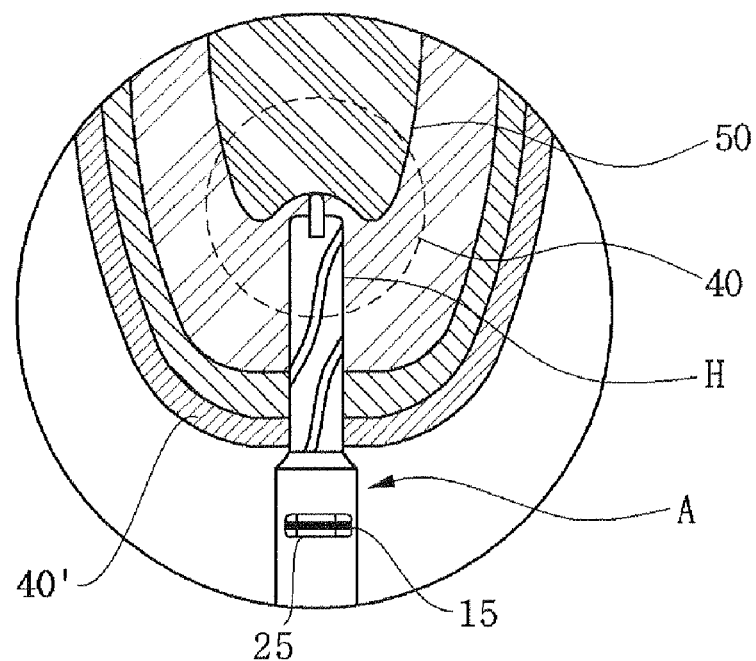
FIG. 4 is a cross-sectional view illustrating the state in which a maxillary sinus floor is drilled using a sinus lift drill (SLD) according to the present invention.
Figure 5:
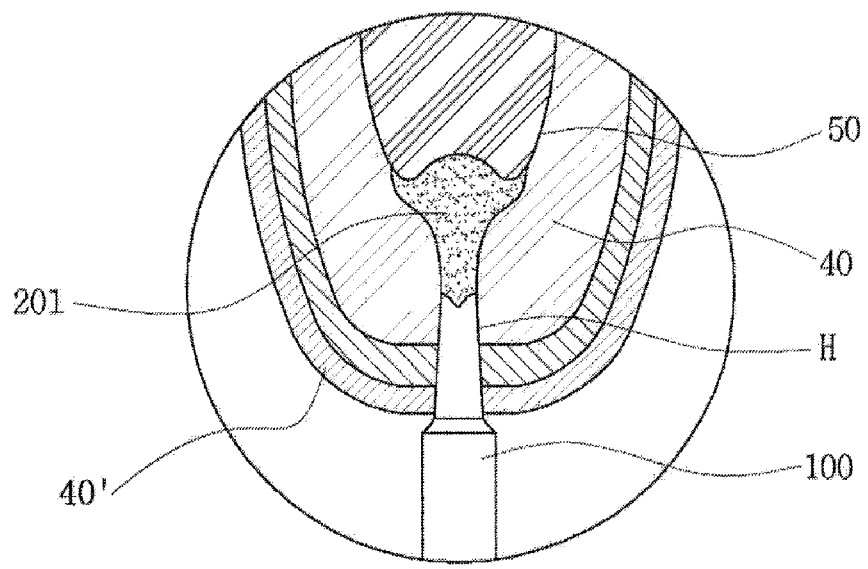
FIG. 5 is a cross-sectional view illustrating the state in which a maxillary sinus membrane is elevated by injecting graft into the same hole with the hydraulic effect according to the present invention.
Figure 6:
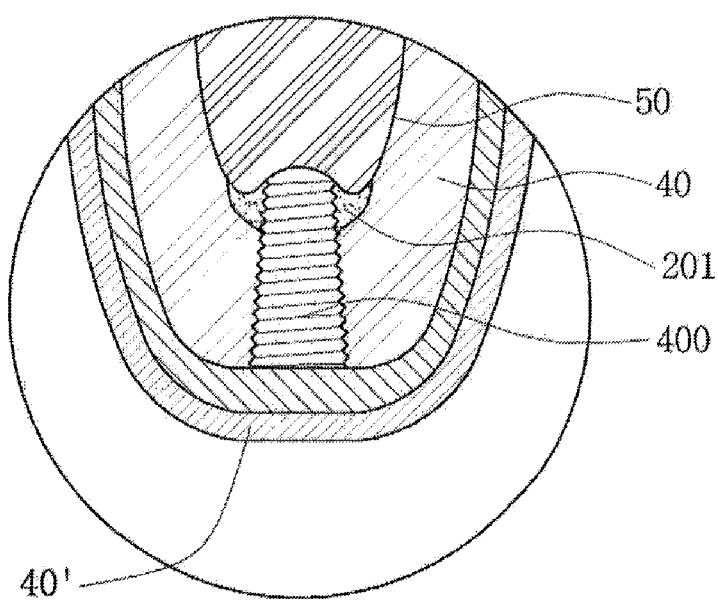
FIG. 6 is a cross-sectional view illustrating the state in which an implant is installed.
Figure 7:
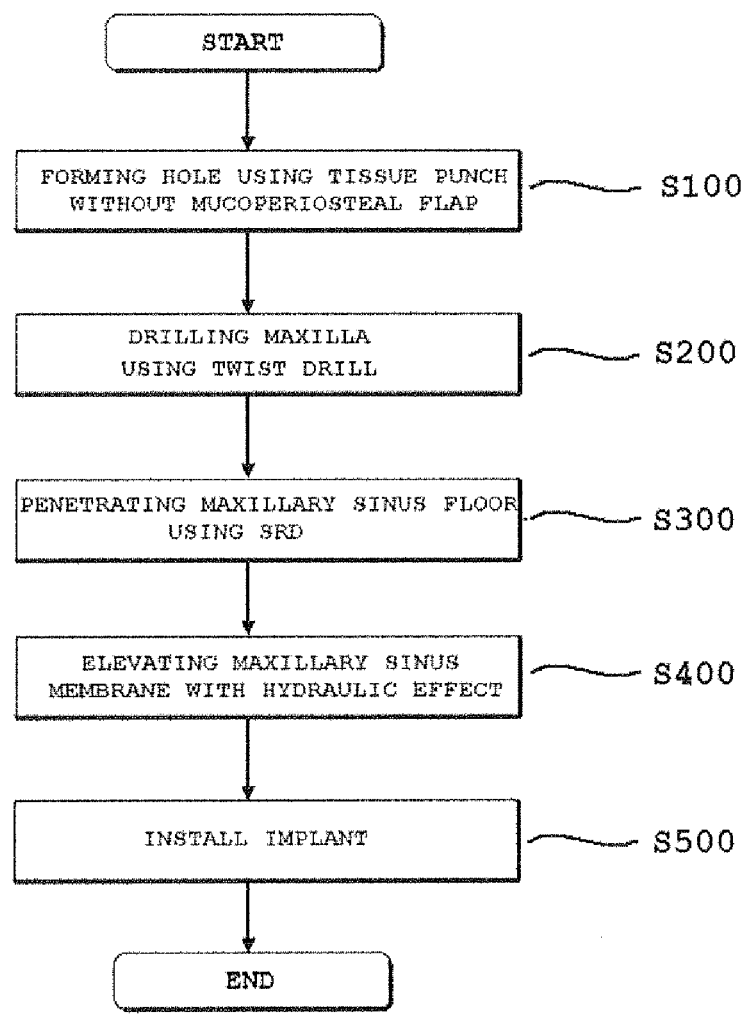
FIG. 7 is a flow chart illustrating a procedure of a maxillary sinus bone graft method using the SLD and hydraulic effect according to the present invention.

FIGS. 1 and 2 are views illustrating the operational states of a drill for forming a hole in the mucoperiosteum according to the present invention; FIG. 3 is a cross-sectional view illustrating the state in which a maxilla is drilled to form a hole by a twist drill according to the common present method; FIG. 4 is a cross-sectional view illustrating the state in which a maxillary sinus floor is penetrated using a sinus lift drill (SLD) according to the present invention; FIG. 5 is a cross-sectional view illustrating the state in which a maxillary sinus membrane is elevated by injecting graft into the same hole with hydraulic effect according to the present invention; FIG. 6 is a cross-sectional view illustrating the state in which an implant is installed; and FIG. 7 is a flow chart illustrating a procedure of a maxillary sinus bone graft method using the SLD and hydraulic effect according to the present invention.

Referring to FIGS. 1 and 2, a hole having a predetermined size (diameter) is formed in the mucoperiosteum 40' covering the maxilla in S100.

A drill A' used to form the hole in the mucoperiosteum 40' can be constructed by a tissue punch drill.

A shank 11' on the top end of a connection shaft 10' is fitted to a head 31' of a dental hand piece 30'. An body of tissue punch drill 20' including the connection shaft 10' is rotated by the actuation of the hand piece 30'.

When the drill A' fitted to the hand piece 30' is brought into close contact with an implantation site and is then caused to rotate, the leading end of the drill blade 23' and the leading end of an annular blade 22' penetrate the mucoperiosteum 40', thereby forming a hole having a predetermined size (diameter) in the mucoperiosteum 40' and exposing the maxilla 40 to the outside.

Accordingly, an implant surgery can be accomplished with a minimized incision size, so that the risk of hematoma is removed and pain and swelling are significantly reduced.

When removing mucoperiosteum of alveolar crest using a tissue punch drill, an implant surgery can be accomplished with a minimized incision size then mucoperiosteal flap procedure, so that the risk of hematoma is removed and pain and swelling are significantly reduced.

In S100, an implant installation site is determined in a predetermined portion of the maxilla 40 in which the drilled hole will be formed.

Next, referring to FIG. 3, a drilled hole H is formed in the installation site using a twist drill 100 in S200.

Specifically, the drilled hole H is primarily formed to a predetermined depth in the implant installation site, and the twist drill 100 used is a 2.0 mm twist drill 100. The drilled hole H may preferably be formed to a depth about 1 mm when the thickness of Bi-cortical bone is less than 3 mm, and to a suitable depth that does not penetrate the bone underlying the maxilla 40 when the thickness of the Bi-cortical bone is 3 mm or more.

Referring to FIG. 4, the maxilla 40 is penetrated without causing damage to the maxillary sinus membrane 50 to a predetermined position by drilling the SLD A through the drilled hole H in S300.

Referring to FIG. 5, the maxillary sinus membrane 50 inside the maxilla 40 is elevated to a predetermined position by injecting graft through the drilled hole H with the hydraulic effect in S400.

Here, the SLD A of the invention is carried into the drilled hole H and is smoothly pressed with a predetermined amount of force in S300.

Then, it can be additionally identified whether or not the inner membrane of the maxilla 40 is bored.

The SLD A can be implemented as any one of implant drills disclosed in Korean Patent Nos. 10-0619145 and 10-0660374.

Figure 8:
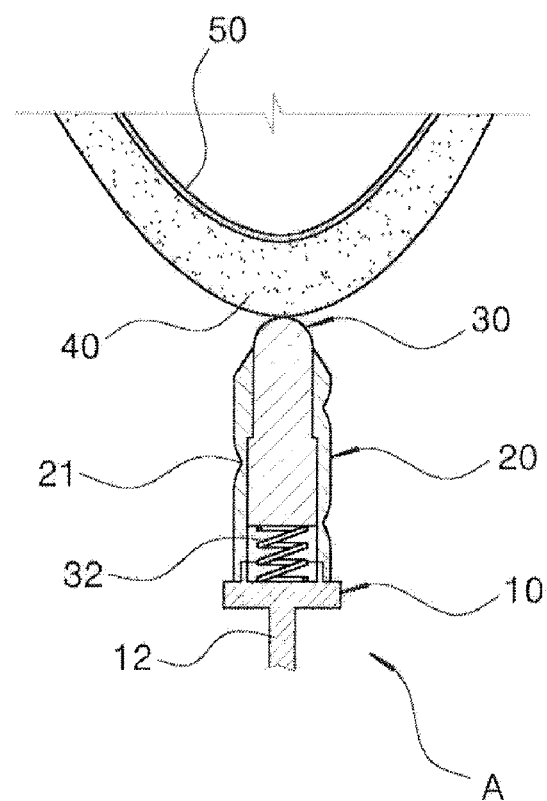
FIGS. 8 to 10 are views illustrating the exemplary operations of the maxillary sinus bone graft method using the SLD and hydraulic effect according to the present invention.
Figure 9:
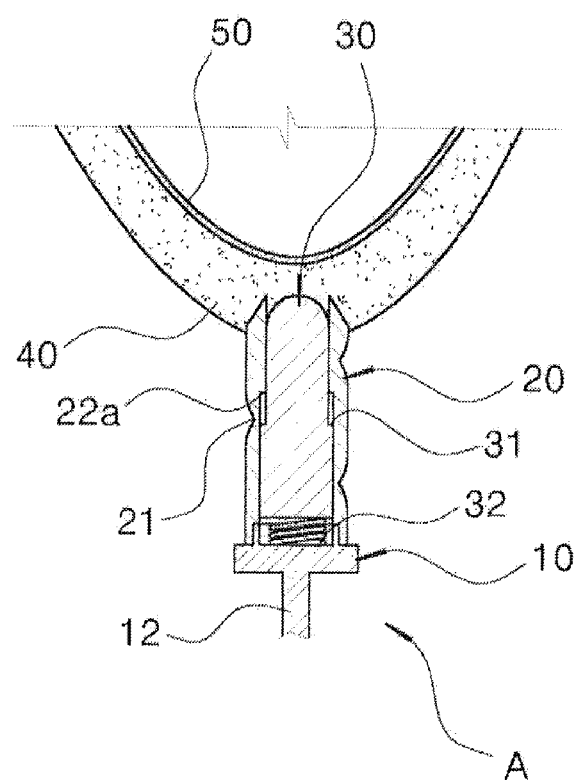
Figure 10:
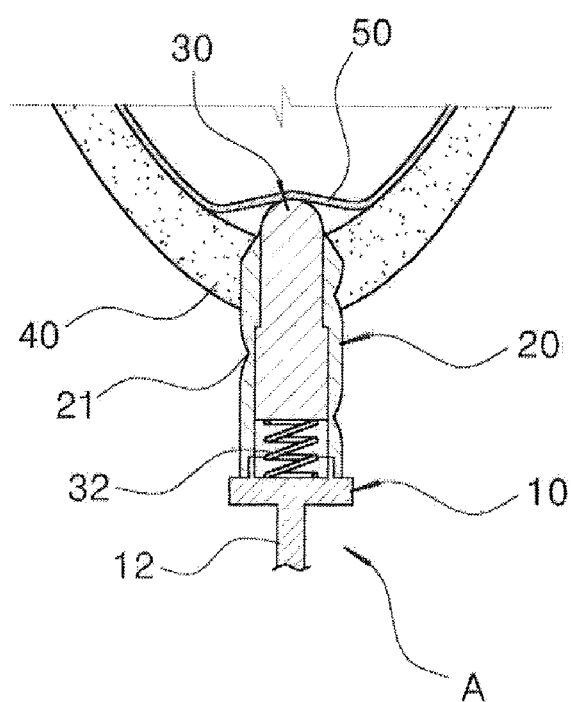

Now, referring to FIGS. 8 to 10, the construction of the SLD adopted in the invention and the operational states thereof will be described.

In the SLD A, the drill blade 20 having cutting grooves 21 is formed on the outer circumference of the cylindrical body 20', and a center shaft having a shank 12 is fitted to a dental hand piece. A protruding member 30 is elastically installed in the body 20' so as to protrude from and retract into the top end of the body 20' in the longitudinal direction of the body 20'. The protruding member 30 is brought into contact with the maxillary sinus membrane 50 of the maxilla 40 to elevate the maxillary sinus membrane 50.

With the SLD A as constructed above, the cylindrical body 20' is introduced through the drilled hole so as to press the maxillary sinus membrane 50 in S300, the drill blade 20 is rotated by pumping to ream the inner circumference of the drilled hole H, and the maxillary sinus membrane 50 is elevated using the protruding-retracting operation of the top end of the protruding member 30.

Referring to FIGS. 4 and 5, the graft 201 is then injected through the drilled hole H into the elevated space defined by the elevated maxillary sinus membrane 50 so that the maxillary sinus membrane 50 is further elevated by the hydraulic effect in S400.

Here, the graft 201, which can be made of a fluid substance, is stored in an amount of 0.3 to 0.5 cc in a syringe 200 having a capacity of 1 cc, a needle is removed from the leading end of the syringe 200, the nozzle of the syringe 200 is brought into contact with the opening of the drilled hole H and is then pressed into the drilled hole H with a predetermined amount of force, and the graft 201 is injected into the drilled hole H.

In the case where the graft 201 is made of material that is not fluid, the graft 201 is mixed with 0.4 cc of a physiological salt solution in a syringe 200 having a capacity of 1 cc, a needle is removed from the leading end of the syringe 200, the nozzle of the syringe 200 is brought into contact with the opening of the drilled hole H and is then pressed into the drilled hole H with a predetermined amount of force, and the graft 201 is injected into the drilled hole H.

Finally, referring to FIG. 6, an implant 400 is installed in the drilled hole H in which the graft 201 is placed in S500.

According to the maxillary sinus bone graft method of the present invention as set forth above, the implant surgery can be rapidly performed in a few minutes. The maxillary sinus bone graft method can be carried out using a simple hand piece without the use of a special tool. Severe pain and edema are considerably mitigated, the amount of bone used (approximately 0.3 cc to 0.5 cc) is merely ⅓ of the lateral approach, and it is possible to obtain Bi-cortical fixation, which is difficult to obtain from the elevation (lifting) by an osteotome.

Further, the maxillary sinus bone graft method of the present invention is safer than all other maxillary sinus elevation methods. Even in the case when the surgery fails and thus has to be done again (five weeks later), it can be carried out easily, safely and quickly.

What is claimed is:

1. A maxillary sinus bone grafting method comprising:
removing mucoperiosteum having a size of a dental implant to be implanted at an alveolar crest area using a tissue punch drill without causing a mucoperiosteal flap,
drilling a maxillary sinus floor without causing damage to a maxillary sinus membrane by inserting a sinus lift drill which has a protruding member in a body of the sinus lift drill so as to protrude from and retract in a longitudinal direction of the body,
elevating the maxillary sinus membrane and injecting a maxillary sinus bone graft adjacent to the drilled maxillary sinus floor; and
installing the dental implant in an inside portion of the drilled maxillary sinus floor,
wherein the step of injecting the graft comprises:
storing the graft in an amount ranging from 0.3 cc to 0.5 cc in a syringe having a capacity of 1 cc;
then removing a needle from a leading end of the syringe;
then bringing a nozzle of the syringe into close contact with an opening of the drilled hole;
then forcing the syringe into the same hole under predetermined pressure; and
then injecting the graft into the same hole.

2. The maxillary sinus bone graft method according to claim 1, wherein the graft is composed of a fluid substance.

3. The maxillary sinus bone graft method according to claim 1, wherein the graft is composed of non-fluid substance.

* * * * *